United States Patent

Morita

[11] Patent Number: 5,596,989
[45] Date of Patent: Jan. 28, 1997

[54] ULTRASONIC PROBE

[75] Inventor: Katsuaki Morita, Tokyo, Japan

[73] Assignee: Olympus Optical Co., Ltd., Tokyo, Japan

[21] Appl. No.: 363,878

[22] Filed: Dec. 27, 1994

[30] Foreign Application Priority Data

Dec. 28, 1993 [JP] Japan .................................. 5-337213

[51] Int. Cl.$^6$ ...................................................... A61B 8/12
[52] U.S. Cl. ................... 128/660.1; 128/662.66; 128/663.01
[58] Field of Search ............ 128/660.01, 660.08–660.1, 128/662.03, 662.06, 663.01

[56] References Cited

U.S. PATENT DOCUMENTS

| | | | |
|---|---|---|---|
| 3,974,475 | 8/1976 | Burkhardt et al. | 340/15 |
| 4,194,510 | 3/1980 | Proudian | 128/660.03 |
| 4,246,791 | 1/1981 | Glenn | 73/620 |
| 4,325,381 | 4/1982 | Glenn | 128/660.1 |
| 4,409,839 | 10/1983 | Taenzer | 128/663.01 X |
| 5,123,418 | 6/1992 | Saurel et al. | 128/662.03 |
| 5,224,174 | 6/1993 | Schneider et al. | 382/5 |
| 5,320,106 | 6/1994 | Tanaka | 128/663.01 X |
| 5,435,314 | 7/1995 | Dias | 128/660.1 X |

Primary Examiner—Francis Jaworski
Attorney, Agent, or Firm—Watson Cole Stevens Davis, P.L.L.C.

[57] ABSTRACT

An ultrasonic probe for performing a scanning of an ultrasonic wave by a reflection mirror is disclosed. The probe comprises an ultrasonic wave generating means formed by a focusing element, an ultrasonic transducer, and an ultrasonic focusing element added to the ultrasonic transducer, a reflecting mirror being a convex ultrasonic mirror for reflecting the ultrasonic wave from the ultrasonic wave generating means or a concave ultrasonic mirror for reflecting the ultrasonic wave from the ultrasonic wave generating means, the distance between the convex ultrasonic mirror and the focusing element and ultrasonic transducer is made shorter than a focal length of the ultrasonic transducer, the distance between the convex ultrasonic mirror and the ultrasonic focusing element added to the ultrasonic transducer is made shorter than a focal length of the ultrasonic focusing element, the distance between the concave ultrasonic mirror and the focusing element and ultrasonic transducer is made longer than a focal length of the ultrasonic transducer, and the distance between the concave ultrasonic mirror and the ultrasonic focusing element added to the ultrasonic transducer is made longer than a focal length of the ultrasonic focusing element.

14 Claims, 7 Drawing Sheets

FIG_1
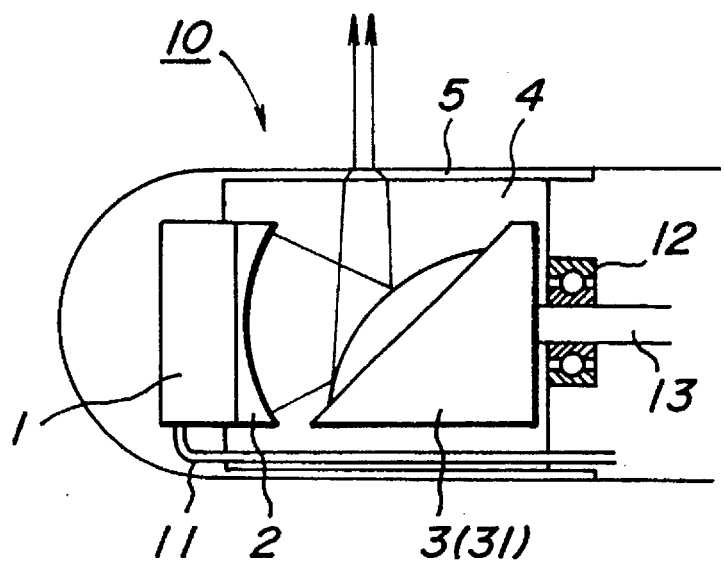
FIG_2
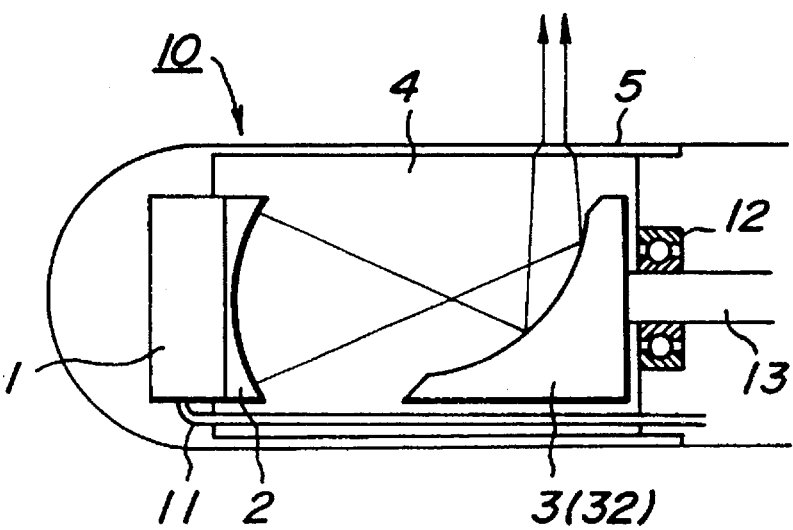

FIG_4
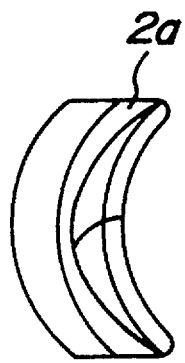
FIG_5
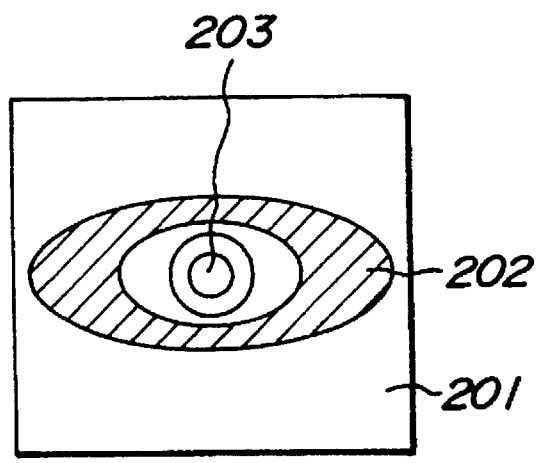

FIG_6
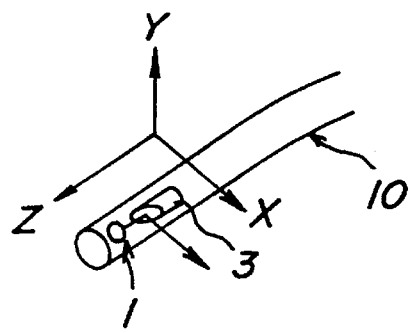
FIG_7
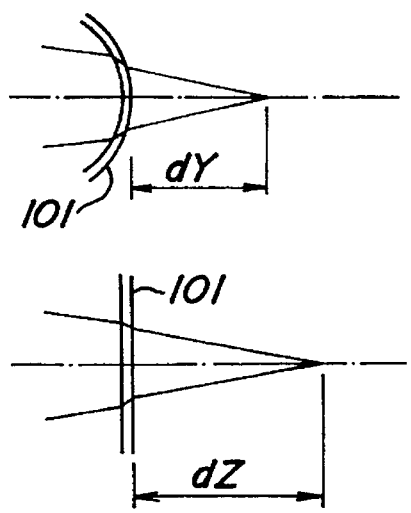
FIG_8
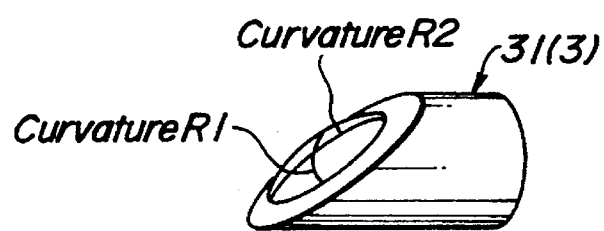

FIG_11
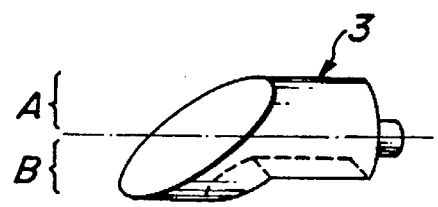
FIG_12
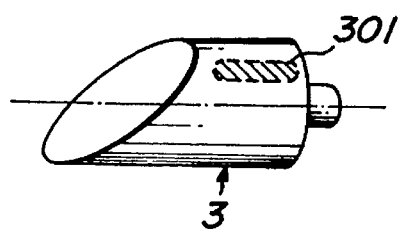
FIG_13
FIG_14
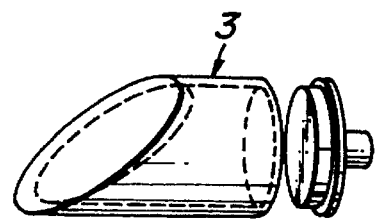

FIG_15
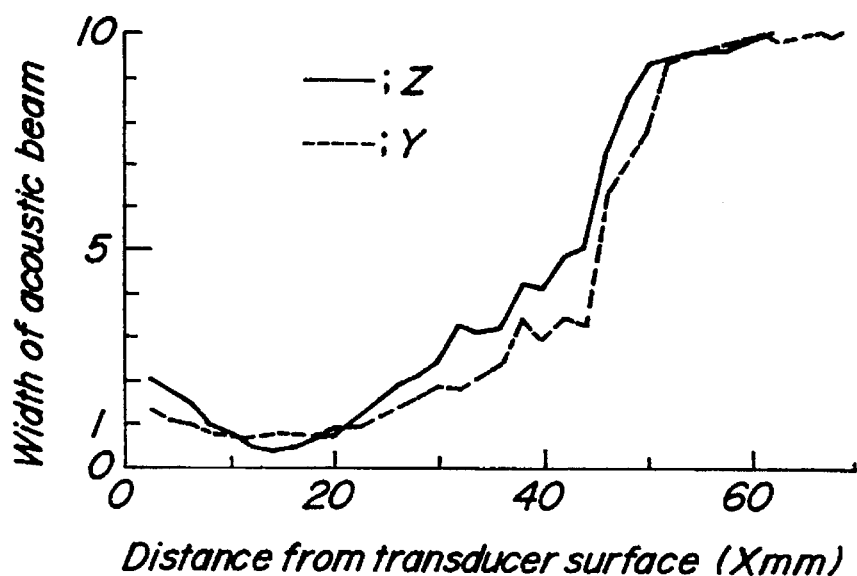
FIG_16
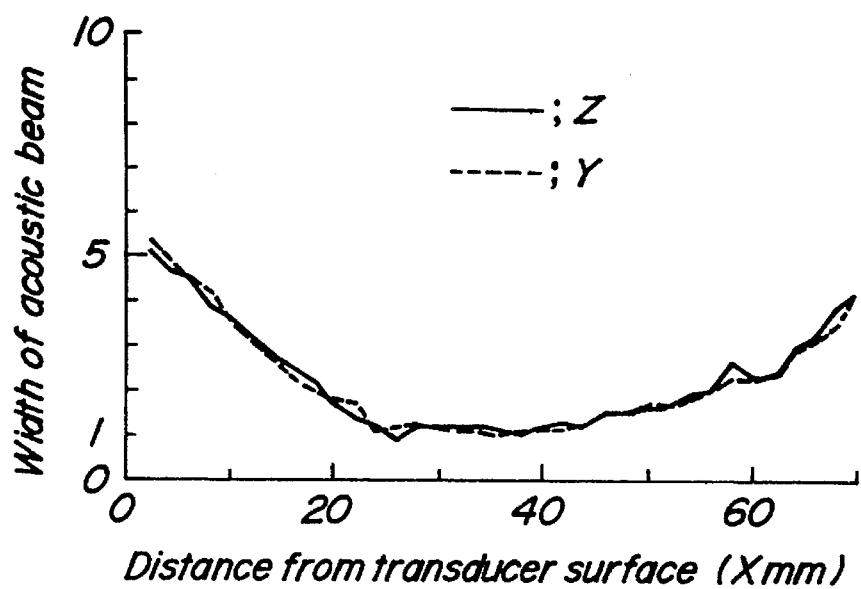

ULTRASONIC PROBE

BACKGROUND OF THE INVENTION

1. Field of the Invention

The present invention relates to an ultrasonic probe, particularly, a medical ultrasonic probe for viewing or imaging sections of a body with a scanning of an ultrasonic beam by a reflecting mirror.

2. Related Art Statement

As a conventional ultrasonic probe of a mechanical radial type, there is a system for scanning the section of the body by ultrasonic energy in such a manner that an ultrasonic transducer is rotatably provided on the tip portion of the ultrasonic probe, to scan it mechanically while rotating the ultrasonic transducer, thereby rotating and scanning it over 360°, or a system for scanning a plane mirror over 360°, in which the ultrasonic energy radiated from an ultrasonic transducer, such as, for example, piezo-electric element, is reflected by a plane mirror (for example, refer to Japanese Patent Application Laid-open NO. 218,144/92).

Such an ultrasonic probe is used in a system apparatus having an image display means or the like.

An ultrasonic probe sector-scanned by swinging it mechanically is disclosed in Japanese Patent Application Laid-open NO. 104,339/90.

It is advantageous that these ultrasonic probe are provided with means for making the radiated ultrasonic beams thinner in order to view areas to be viewed of a subject body with high resolution.

It is ideal to obtain the ultrasonic probe in such a manner that a uniformly thin ultrasonic beam is formed. However, since it is technically difficult to form such an ideal ultrasonic probe, an acoustic lens is attached to the surface of the utilized transducer, or a curved mirror is used to obtain the ultrasonic beam with high resolution by focusing the ultrasonic wave on the areas to be viewed in the ultrasonic probe combined with the above system device.

However, if a concave acoustic lens or a concave mirror is utilized separately, an excellent image can be obtained with high resolution at focal point of the ultrasonic beam, but the ultrasonic beam becomes thick at its off-focal points, thereby decreasing resolution.

In the case of an ultrasonic endoscope, particularly, if the areas near the center of the endoscope are to be viewed with high resolution, the curvature of the acoustic lens or the concave mirror for the ultrasonic transducer is made small, thereby setting the focus of the beam near the probe.

FIG. 15 is an explanatory view showing the conditions of such an acoustic beam, in which the width of the acoustic beam is plotted to the distance from the transducer surface. That is, an abscissa is plotted as the distance from the transducer surface, and an ordinate is plotted as the width of the acoustic beam. As shown from FIG. 15, if the focus becomes near, minimum beam diameter becomes comparatively small, but the focal depth becomes shallow, so that the resolution becomes inferior without near the focus, and thus the sensitivity becomes low, thereby decreasing the image quality remarkably.

As seen from the above result, even if the acoustic lens and the concave mirror for the transducer are only accommodated in the ultrasonic probe as a constituent element, and set as described above, the diameter of whole beam is thin, so that the ultrasonic probe having high resolution which is not influenced by the distance from the probe can not be obtained.

If the areas far from the center of the endoscope must be observed with high resolution, the curvatures of the acoustic lens and the concave mirror are made large and the focus thereof is set far in the distance.

The characteristic diagram exhibiting the shape of the acoustic beam is shown in FIG. 16. In the case of this embodiment, if the focus is situated in far distance, the diameter (thickness) of the ultrasonic beam in comparatively far distance becomes substantially unity, but the diameter of the minimum beam in focus point can not be made small, thereby obtaining an image having substantially inferior resolution.

In this case, an improving method at the side of ultrasonic probe has a certain limit, so that the ultrasonic probe capable of observing the subject body with high resolution irrespective of the distance from the probe near distance to far distance thereof can not be realized.

The method of widening the focus depth with various technics has been tried, but this method require the change or modification of the system, and can not be realized easily. That is, any method requires large and complicated electric circuit, and thus large ultrasonic transducer is required, so that this method can not be realized easily in the ultrasonic probe.

SUMMARY OF THE INVENTION

It is an object of the present invention to eliminate the above described disadvantages of the conventional ultrasonic probe.

It is another object of the present invention to provide an ultrasonic probe with simple construction in which the subject body can be observed with high resolution from near distance to far distance of the probe, and having deep focus depth.

According to the present invention, there is provided an ultrasonic probe for performing a scanning of an ultrasonic wave by a reflection mirror comprising an ultrasonic wave generating means having an ultrasonic transducer, a focusing element for focusing the ultrasonic wave generated from the ultrasonic wave generating means, a reflecting mirror for reflecting the ultrasonic wave from the focusing element, wherein the distance between the focusing element and the reflecting mirror is so determined that a focusing depth is large and an observation is possible with high resolution from near distance to far distance of the probe.

In an embodiment of the ultrasonic probe according to the present invention, the ultrasonic wave generating means is formed by a focusing element and ultrasonic transducer, or an ultrasonic focusing element added to the ultrasonic transducer.

In a preferable embodiment of the ultrasonic probe according to the present invention, the reflecting mirror is a convex ultrasonic mirror for reflecting the ultrasonic wave from the ultrasonic wave generating means, or a concave ultrasonic mirror for reflecting the ultrasonic wave from the ultrasonic wave generating means.

In a further preferable embodiment of the ultrasonic probe according to the present invention, the distance between the convex ultrasonic mirror and the focusing element and ultrasonic transducer is made shorter than a focal length of the ultrasonic transducer. The distance between the convex ultrasonic mirror and the ultrasonic focusing element added to the ultrasonic transducer is made shorter than a focal length of the ultrasonic focusing element. The distance between the concave ultrasonic mirror and the focusing element and ultrasonic transducer is made longer than a focal length of the ultrasonic transducer. The distance between the concave ultrasonic mirror and the ultrasonic focusing element added to the ultrasonic transducer is made longer than a focal length of the ultrasonic focusing element.

The focusing element is an acoustic lens having aspheric surface. The convex ultrasonic mirror is aspherical mirror having two different curvatures, and one curvature is larger than the other curvature. The concave ultrasonic mirror is aspherical mirror having two different curvatures, and one curvature is smaller than the other curvature. The reflection mirror has a central axis of rotation passing through a center of gravity of the mirror.

According to the present invention, at the stage of radiating the ultrasonic beam from the ultrasonic probe, the shape of the ultrasonic beam is effectively improved by sufficiently focusing the beam, and making the beam parallel to the acoustic axis, thereby obtaining an ultrasonic probe having simple construction without using large and complicated electric circuit, and capable of making the diameter of whole beam small, so that the probe with high resolution which is not effected by the distance from the probe can easily realized.

BRIEF DESCRIPTION OF THE DRAWINGS

FIG. 1 is an explanatory view showing first embodiment of an ultrasonic probe according to the present invention, in which the construction of the probe tip portion is shown;

FIG. 2 is an explanatory view showing embodiment of an ultrasonic probe according to the present invention, in which the construction of the probe tip portion is shown;

FIG. 4 is a side view showing another embodiment of the acoustic lens capable of applying it in the case of adding the acoustic lens to the ultrasonic probe;

FIG. 5 is a plan view showing one example of the ultrasonic image obtained in case of using the acoustic lens;

FIG. 6 is a perspective view showing the explanation of setting of a coordinate system;

FIG. 7 is a plan view showing the explanation of causing the difference of focus positions in Y direction and Z direction in the coordinate system;

FIG. 8 is a perspective view showing a first example of the construction of the ultrasonic mirror used together with the ultrasonic probe shown in FIG. 1 or FIG. 2;

FIG. 11 is a perspective view showing a fourth example of the construction of the ultrasonic mirror used together with the ultrasonic probe shown in FIG. 1 or FIG. 2;

FIG. 12 is a perspective view showing a fifth example of the construction of the ultrasonic mirror used together with the ultrasonic probe shown in FIG. 1 or FIG. 2;

FIG. 13 is a perspective view showing a sixth example of the construction of the ultrasonic mirror used together with the ultrasonic probe shown in FIG. 1 or FIG. 2;

FIG. 14 is a perspective view showing a seventh example of the construction of the ultrasonic mirror used together with the ultrasonic probe shown in FIG. 1 or FIG. 2;

FIG. 15 is an explanatory view showing the result of experiment of the ultrasonic probe shown in FIG. 1, that is, characteristic of the acoustic beam to the distance from the transducer surface in order to exhibit the improvement of beam shape; and FIG. 16 is an explanatory view showing the result of experiment of the ultrasonic probe shown in FIG. 1, that is, characteristic of the acoustic beam to the distance from the transducer surface in order to exhibit the improvement of beam shape.

DETAILED EXPLANATION OF THE PREFERRED EMBODIMENT

Figure 3:
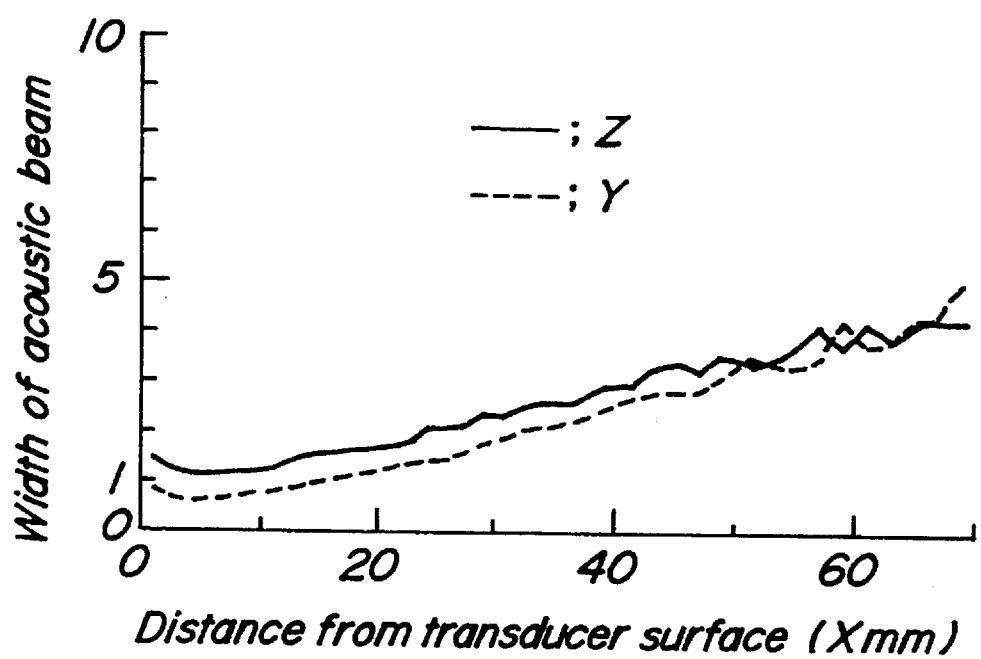
FIG. 3 is an explanatory view showing the result of experiment of the ultrasonic probe shown in FIG. 1, that is, characteristic of the acoustic beam to the distance from the transducer surface in order to exhibit the improvement of beam shape.

Now to the drawings, there are shown various embodiments of an ultrasonic probe according to the present invention. Like parts are shown by corresponding reference characters throughout several views of the drawings.

FIGS. 1 and 2 show first and second embodiments of an ultrasonic probe according to the present invention. In these figures, there are shown the constructions of a tip portion of the ultrasonic probe of a mechanical radial mirror reflection type, in which a mirror is rotated to performing a scanning of areas of a subject body to be observed.

At first, the ultrasonic probe shown in FIG. 1 is explained (first embodiment). In this embodiment, a concave mirror is used as the ultrasonic mirror. In FIG. 1, an ultrasonic transducer 1 is provided to the tip portion of the ultrasonic probe 10. The ultrasonic transducer 1 is formed by a piezo-electric element, and the oscillating direction of the piezo-electric element is set to direct to the axial direction (the central axis direction) of the ultrasonic probe 10.

In this embodiment, a concave acoustic lens 2 is adhered to the surface of the ultrasonic transducer 1 as a first ultrasonic focusing element. In this way, the ultrasonic probe 10 has the concave acoustic lens 2 connected to the ultrasonic transducer 1 as the focusing element therefor.

As shown in FIG. 1, in this embodiment, a convex ultrasonic mirror 31 being the ultrasonic mirror 3 is displaced at (the transducer side than) the focus of the concave acoustic lens 2 as a second focusing element. The convex acoustic mirror 31 is so formed that a convex mirror is formed on at least a part of the surface which reflects the ultrasonic wave generated by driving the transducer 1.

The ultrasonic wave reflected by the convex ultrasonic mirror 31 is delivered through an acoustic medium 4 and an acoustic window 5.

The transmission and the reception of the ultrasonic signal for the ultrasonic probe 10, and the rotating drive of the ultrasonic mirror 31 may fundamentally be performed by conventional techniques. A signal transmitting cable 11 is connected to the ultrasonic transducer 1, and the ultrasonic mirror 3 is attached to a rotating member 13 supported by a bearing 12, in such a manner that it is rotated and driven.

The ultrasonic probe 10 is a mechanical ultrasonic probe capable of scanning it by rotating a mirror, and comprises the ultrasonic transducer 1 displaced in such a manner that the oscillating direction of the piezo-electric element is directed to the axial direction of the ultrasonic probe, the concave acoustic lens 2 provided to connect to the ultrasonic transducer 1, and the convex acoustic mirror 31. In case of adding the concave acoustic lens 2 to the ultrasonic transducer 1 as a focusing element, and the convex ultrasonic mirror 31 is used as the ultrasonic mirror 3, the ultrasonic generating unit and the ultrasonic mirror are so arranged and set that the distance between the convex mirror 31 and the concave acoustic lens 2 on the acoustic axial is made shorter than the focal length of the concave acoustic lens 2.

In the above construction, in observing with the endoscope inspection, the ultrasonic wave is generated by driving the ultrasonic transducer 1 by the pulse signals outputted from the pulse generator (not shown). The ultrasonic wave is focused by the concave acoustic lens 2 of the transducer surface, reflected by the convex mirror 31, and radiated in the direction of 90° to the center axis of the endoscope through the acoustic medium 4 and the acoustic window 5.

In this embodiment, the scanning of the ultrasonic wave is performed by rotating the convex ultrasonic mirror 31. That is, the convex ultrasonic mirror 31 is rotated by the rotating member 13 to perform the 360° scanning, thereby forming an ultrasonic image.

In this way, the endoscope observation of the areas to be inspected is performed. In this case, according to the present embodiment, the ultrasonic generating unit and the convex ultrasonic mirror 31 are so arranged and set that the distance between the convex ultrasonic mirror 31 and the concave acoustic lens 2 as the ultrasonic focusing element added to the ultrasonic transducer 1, is made shorter than the focal length of the concave acoustic lens 2, so that the observation can be performed with high resolution from the near distance to far distance to the ultrasonic probe. This observation can be performed by the ultrasonic probe 10 having large focal depth and with simple construction.

The aim of the present invention can be realized by the fact that the ultrasonic beam satisfy the following conditions ① and ② at the stage that the ultrasonic wave is radiated from the ultrasonic endoscope.

① When the ultrasonic beam passes through the acoustic window 5, the beam must be focused sufficiently.

② The acoustic beam must be made collimatedly with respect to the acoustic axis.

In order to satisfy the above condition ①, this embodiment utilizes the ultrasonic transducer 1 connected to the acoustic lens 2 having small curvature. However, if this acoustic lens 2 is used as it is, the ultrasonic beam is focused near the probe 10, and diverged at the far distance. In this embodiment, then in addition to this acoustic lens 2, the above described convex mirror 31 is used as a deflection mirror, this mirror is arranged as described above, thereby correcting the beam converged by the acoustic lens 2 so as to obtain a beam collimated to the acoustic axis.

In this way, at the stage of radiating the ultrasonic beam from the ultrasonic probe, the shape of the ultrasonic beam is effectively improved by sufficiently focusing the beam, and making the beam parallel to the acoustic axis, thereby obtaining an ultrasonic probe having simple construction without using large and complicated electric circuit, capable of making the diameter of whole beam small, so that the probe with high resolution which is not effected by the distance from the probe can easily realized.

In order to correct or collimate the beam narrowed down by the concave acoustic lens 2, to the acoustic axis by the convex ultrasonic mirror 31, SR of the acoustic lens 2 and the convex mirror 31 must be adjusted so as to focus the beam at far distance, since the ultrasonic beam parallel to the acoustic axis has a property that the beam itself is diverged.

FIG. 3 is a characteristic view of the acoustic beam width showing the shape of the beam based on the experimental result of the ultrasonic probe built as a trial according to the first embodiment.

In this experimental result, in the same manner as the examples shown in FIGS. 15 and 16, the abscissa is plotted as the distance X mm (refer to the coordinate system in FIG. 6) from the transducer surface, and the ordinate is plotted as the width of the acoustic beam. In the experimental result, the concave acoustic lens 2 and the convex ultrasonic mirror 31 had SR of 7, 22, respectively.

As is seen from the experimental result shown in FIG. 3, it was found that the shape of the ultrasonic beam is improved to obtain the ultrasonic probe having thin width of whole beam irrespective of the distance from the probe 10, even when it is compared from width of the acoustic beam to the distance (X mm) in FIG. 15 in the case of observing the areas of the body near from the center of the endoscope with high resolution, and even when it is compared from width of the acoustic beam to the distance (X mm) in FIG. 16 in the case of observing the areas of the body far from the center of the endoscope with high resolution.

In FIG. 3, the characteristic of the probe 10 in the center axis direction (Z axis direction (refer to the coordinate system in FIG. 6)) is shown by solid line, and the characteristic of the probe 10 in the azimuthal direction (Y axis direction (refer to the coordinate system in FIG. 6)) is shown by dashed line (the same as in FIGS. 15 and 16). These two beam characteristics in FIG. 3 are also described later.

In the above described experimental result, SR was selected as 7, 22, respectively, so that the acoustic field formed by the ultrasonic transducer was shifted from the logical calculation based on the Snell laws. In order to compensate this shift, the ultrasonic focusing element and the ultrasonic mirror are designed in such a manner that the ultrasonic beam is focused at the distance of 50 mm (=X) from the center of the endoscope, but the focus is too near the probe, so that the width of the acoustic beam becomes diverged at far distance. It can be, however, well assumed from the above experimental result that the shape of the ultrasonic beam may be improved by adjusting SR of the transducer side and the convex mirror side.

Then, the second embodiment of the ultrasonic probe according to the present invention is explained.

The ultrasonic probe of the above first embodiment shown in FIG. 1 was comprised of the first ultrasonic focusing element connected to the ultrasonic transducer, and the convex ultrasonic mirror, the distance between the convex mirror and the first ultrasonic focusing element is made shorter than the focal length of the first ultrasonic focusing element, thereby improving the shape of the beam. The present embodiment is a mechanical ultrasonic probe for scanning the ultrasonic beam by rotating the mirror, and comprises an ultrasonic transducer placed to direct the oscillating direction of a piezo-electric element to an axial direction of an ultrasonic probe, a first ultrasonic focusing element connected to the ultrasonic transducer and a concave ultrasonic mirror, the distance between the concave ultrasonic mirror and the ultrasonic focusing element is made longer than the focal length of the first ultrasonic focusing element, thereby realizing the same aim as that of the first embodiment.

The subject matter of the ultrasonic probe of the present embodiment is explained with reference to FIG. 2.

In the above first embodiment, the reflection surface of the mirror is set to place at the transducer side than the focus (concretely, the focus of the concave acoustic lens 2 as the ultrasonic focus element) at the side of the ultrasonic transducer 1, but, for example, it is also considered that the distance between the transducer 1 and the reflection mirror is longer than the focal length of the transducer.

In this case, in order to make the ultrasonic beam so as to satisfy the above conditions ① and ②, it is necessary to use a concave mirror instead of the convex mirror 31 as a second focusing element, so that the probe adopts the construction shown in FIG. 2.

That is, in this embodiment, a concave acoustic lens 2 is attached to the surface of the ultrasonic transducer 1 at the tip portion of the ultrasonic endoscope as a first focusing element, but on the contrary to the construction shown in FIG. 1, a concave ultrasonic mirror 32 as a second focusing element is placed at the position exceeding the focus position of the concave acoustic lens 2 as shown in FIG. 2.

In this way, in the case that the ultrasonic mirror has the concave mirror 32, the ultrasonic probe is so constructed that the distance between the concave mirror and the concave acoustic lens 2 attached to the ultrasonic transducer 1 is made longer than the focal length of the concave acoustic lens 2.

The other construction is the same as that of the probe shown in FIG. 1, so that its detailed explanation is omitted.

In this embodiment, also the ultrasonic beam is formed so as to satisfy the above conditions ① and ②, and thus the same function and effect as that of the first embodiment can be obtained, so that the shape of the ultrasonic beam can be improved to obtain the ultrasonic probe having thin width of whole beam irrespective of the distance from the probe 10, with high resolution.

In the first and the second embodiments, the construction utilizing the concave acoustic lens 2 connected to the surface of the ultrasonic transducer 1 as a ultrasonic focusing element, is provided, but the present invention is not limited to the above construction.

That is, a construction of combining the ultrasonic transducer and a focusing element by using the transducer itself as a concave transducer, can be provided, so that respective embodiments have a construction using such an ultrasonic transducer itself or first ultrasonic focusing element connected to the ultrasonic transducer (for example, the concave acoustic element shown in FIGS. 1 and 2).

In this case, the same function and effect as that of the first embodiment can be realized, so that the ultrasonic probe can be obtained capable of observing the areas of the body with high resolution from near position to far position of the probe, with simple construction and with large focal depth.

Therefore, the present invention comprises the concave or the convex ultrasonic mirrors (31 or 32). When it comprises the convex mirror 31, the distances between the convex mirror 31 and the transducer, or between the convex mirror 31 and the focusing element are made shorter than that of the transducer or the focal element. When it comprises the concave mirror 32, the distances between the mirror 32 and the transducer, or between the mirror 32 and the focusing element are made longer than that of the transducer or the focusing element.

Next, further embodiment of the ultrasonic probe according to the present invention (a third embodiment or the like) is explained with respect to FIG. 4, or the like.

In the following respective embodiments, the basic construction of the ultrasonic probe is substantially the same as that of the first or the second embodiment shown in FIG. 1 or FIG. 2, so that its detailed explanation is omitted, and the subject matter of respective embodiments is only explained.

In the first and the second embodiments as well as the modifications thereof, as shown in FIG. 4, if the shape of acoustic lens of the ultrasonic transducer is made to be an aspheric surface lens 2a, according to the rotation of the the ultrasonic mirror 3 (31 or 32), the incident angle of the acoustic beam which is incident on the ultrasonic mirror is changed, so that as shown in FIG. 5, the ultrasonic endoscope having different focus regions 202 according to the azimuth or direction viewed from an image center 203 on the ultrasonic image 201 observed by a display means at the system side can be constructed by the present ultrasonic probe.

If such an endoscope is realized, the observation registering the areas to be observed on the high resolution can be realized by twisting the endoscope. For example, in the medical field, the present ultrasonic probe can be applied to the areas that the distance between the probe and the wall of the esophagus, and the areas that whole image must be observed by having some distance between the endoscope and the wall of the stomach.

Next, the coordinate is considered as shown in FIG. 6.

In FIG. 3, the experimental result of the improvement of the beam shape based on the first embodiment was shown, but two beam shapes (solid line and dashed line) of the experimental result shows the beam width in the Z direction and beam width in the Y direction are shown in the coordinate system.

In this figure, it can be conformed that these beam shapes are compared, the beam width in the Z direction is always substantially wider than the beam width in the Y direction. Since the acoustic beam has an ellipsoidal section due to the astigmatism inevitably caused by the reflection of the focused ultrasonic wave of the concave acoustic lens 2 on the convex ultrasonic mirror 31. Therefore, the beam in the Z direction becomes thick, resulting in a factor of decreasing the image quality of the ultrasonic image thus formed.

As shown in the upper portion and the lower portion of FIG. 7, since the tip housing 101 of the acoustic window of the ultrasonic endoscope has a hollow cylinder, differences is arises between the focal position in the Y direction and the focal difference in the Z direction as shown by dY and dZ, respectively.

Then, the method of compensating such an acoustic beam can be realized by a next embodiment (a third embodiment) shown in FIG. 8.

In this embodiment, to this end, the utilized ultrasonic mirror itself is made to have an aspheric surface, thereby making the curvature R1 and the curvature R2 different to each other. That is, as shown in FIG. 8, taking into consideration that in the convex ultrasonic mirror 31, the beam shape in the Y direction is dependent on the curvature R1, and the beam shape in the Z direction is dependent on the curvature R2, the beam in the Z direction is made thinner by taking R of the curvature R2 larger than that of the curvature R1, so that the beam section can be made more circular.

The same means can be applied to the probe shown in the second embodiment.

Figure 9:
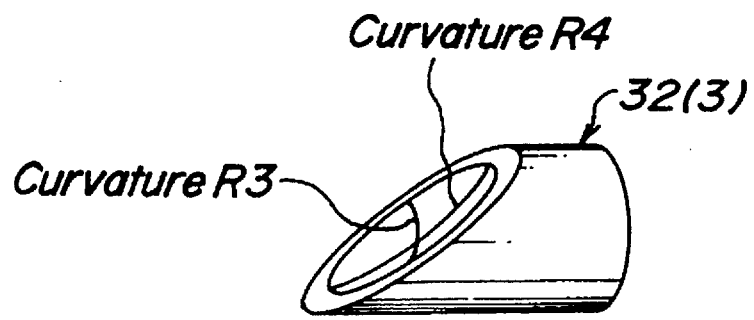
FIG. 9 is a perspective view showing a second example of the construction of the ultrasonic mirror used together with the ultrasonic probe shown in FIG. 1 or FIG. 2.

Such an embodiment is shown in FIG. 9 as a fourth embodiment.

As shown in FIG. 9, in the concave ultrasonic mirror 32, the feature of making a curvature R4 smaller than a curvature R3 can be made the acoustic beam width in the Z direction more decreased, and thus the beam section can be made more circular.

Figure 10:
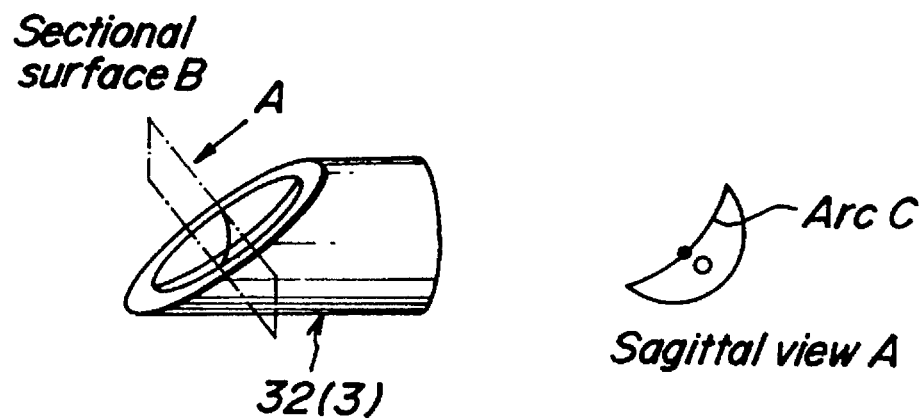
FIG. 10 is a perspective view showing a third example of the construction of the ultrasonic mirror used together with the ultrasonic probe shown in FIG. 1 or FIG. 2.

Next, a further embodiment in which the ultrasonic mirror is made to have an aspheric surface, is shown in FIG. 10.

In the third embodiment and the fourth embodiment, the astigmatism is considered. However, not only the astigmatism, but also spherical aberration are affected on the beam shape. That is, there is a phenomenon that the ultrasonic wave reflected near the center portion of the curved mirror is focused at far a farther point than the ultrasonic wave reflected near the peripheral portion of the curved mirror, so that the curved mirror does not decrease the width of the beam at the focus point, completely, so that the minimum beam width is limited at this focus point.

Then, as shown in FIG. 10, the present embodiment (fifth embodiment) provides an ultrasonic probe in which the curved surface of the concave ultrasonic mirror 32 is made to be an aspheric surface mirror designed by considering reflection conditions instead of spheric surface. In this way, the focal positions of the ultrasonic waves reflected on the center portion and the peripheral portion of the transducer can be coincident with each other, so that the beam shape that is, the resolution of the ultrasonic image can be improved.

Concretely, in the concave ultrasonic mirror 32 in the embodiment shown in FIG. 10, when the section B of the mirror is viewed from the direction A, as shown at right side, the arc C does not become a circular arc, the construction in which R becomes smaller from the center O to the periphery, so that the beam shape due to the coincidence with the focal position, that is, resolution of the ultrasonic image can be improved.

Then, a further embodiment of the ultrasonic probe according to the present invention is explained with respect to FIGS. 11 to 14.

As described above, according to the present invention, it is found that the feature of using the ultrasonic mirror 3 as one of acoustic focusing element plays a role in the improvement of the beam shape.

However, in the above ultrasonic mirror 3 (the convex ultrasonic mirror 31, the concave ultrasonic mirror 32), mass distribution is apt to become uneven, as shown in FIGS. 1, 2, 8, 9 and 10 or the like. That is, the center of gravity of the mirror does not place on the center axis of the mirror, so that even if the center axis of the mirror is rotated by coupling it to the rotating power, the irregular rotation arises.

Then, this irregular rotation can be preferably canceled by the compensation that the axis of the rotating center of the mirror passes through the center of gravity of the mirror.

These means are shown in respective embodiment of FIGS. 11 to 14.

As one means, as shown in FIG. 11, the base portion 3a at the heavy portion shown by B of the ultrasonic mirror 3 (31 or 32) as a second acoustic focusing element in the first and the second embodiments is made cut away as shown, and the mass distribution of the light portion A and the heavy portion B can be adjusted therebetween.

As the other means, following means are considered. That is, means for burying the member such as for example a heavy metal 301 into the light portion A (the upper portion in FIG. 12 as in the same in FIG. 11) of the ultrasonic mirror 3, as shown in FIG. 12, the means for shifting the rotating center of the ultrasonic mirror 3 forcedly, and placing the center of gravity of the mirror on the rotating axis, as shown in FIG. 13, and means for making the ultrasonic mirror 3 itself hollow, thereby making the mass of the mirror light, resulting in a small effect of the eccentricity, as shown in FIG. 14.

If the diameter of the mirror is short, the measure for the irregular rotation shown in FIGS. 11, 12, 13 and 14 may not always be performed, so there will be no difficulty in its generation of the ultrasonic image. Therefore, this measure may not be performed. However, if the diameter of the utilized reflection mirror becomes large, such as the probe used in the ultrasonic endoscope, the effect of the rotating mirror becomes large in proportion to the third power of increase in diameter of the mirror, so that the measure becomes inevitable element, and thus it is effective in such a case.

Even if the diameter of the mirror is small, such a measure may be performed according to the above embodiment.

Moreover, the embodiment rather than that shown in FIGS. 11 to 14 may also be used.

As a power source for rotating the ultrasonic mirror 3 (31 or 32), a system for transmitting the power to the tip portion of the probe by the flexible shaft has been utilized, but a small electric motor is accommodated in the tip portion of the endoscope, so that a compact endoscope can be obtained. In this case, a rotating member 13 shown in FIG. 1 or 2 may be made a rotating shaft of the accommodated motor.

However, utilized motor itself capable of accommodating it in the tip portion of the endoscope must be selected, so that the output power is also small. Even if any kind of the motor is used, it is impossible to rotate the motor at the position of T-N (torque-revolution number) curve with superior efficiency in order to ensure necessary torque and revolution number, so that the motor must be driven at the high torque side with inferior efficiency. Particularly, there is a tendency that the efficiency of the motor becomes inferior at the starting.

Then, the next countermeasure is effective.

That is, in the above case, the motor driving circuit for an image freezing circuit and its accommodated motor is made independent, so as not to stop the motor at the image freezing, thereby minimizing the times for rotating the motor with inferior efficiency at starting.

In the present invention, the above countermeasure may be carried out by the above means.

Moreover, in the embodiments on and after FIG. 4, respective embodiments are explained separately, but it may be carried out with combination of all embodiments or two or more embodiments.

The present invention is not limited to the above embodiments, modifications, improvements or the like.

For example, the scanning of the ultrasonic beam is performed by rotating the ultrasonic mirror, but the present invention may be applied to a mechanical scanning ultrasonic probe in which the scanning is performed by swinging the mirror, or the other probe.

What is claimed is:

1. An ultrasonic probe comprising:

an ultrasonic wave generating means, having an ultrasonic transducer, for generating an ultrasonic wave;

a focusing element, having a first non-zero focusing power, for focusing the ultrasonic wave generated by the ultrasonic wave generating means to produce a focused ultrasonic wave; and a reflecting mirror, disposed in a path of the focused ultrasonic wave and having a second non-zero focusing power, for reflecting the focused ultrasonic wave to produce a reflected ultrasonic wave;

wherein the first non-zero focusing power, the second non-zero focusing power and a distance between the focusing element and the reflecting mirror are selected so that the reflected ultrasonic wave is substantially collimated as the reflected ultrasonic wave exits the ultrasonic probe.

2. An ultrasonic probe as claimed in claim 1, wherein the focusing element comprises an ultrasonic lens disposed in a path of the ultrasonic wave generated by the ultrasonic wave generating means.

3. An ultrasonic probe as claimed in claim 2, wherein the ultrasonic lens is attached to a face of the ultrasonic transducer from which the ultrasonic wave is emitted.

4. An ultrasonic probe as claimed in claim 3, wherein the reflecting mirror is a convex ultrasonic mirror, and said distance is made shorter than a focal length of the ultrasonic lens.

5. An ultrasonic probe as claimed in claim 3, wherein the reflecting mirror is a concave ultrasonic mirror, and said distance is made longer than a focal length of the ultrasonic lens.

6. An ultrasonic probe as claimed in claim 2, wherein the reflecting mirror is a convex ultrasonic mirror, and said distance is made shorter than a focal length of the ultrasonic lens.

7. An ultrasonic probe as claimed in claim 2, wherein the reflecting mirror is a concave ultrasonic mirror, and said distance is made longer than a focal length of the ultrasonic lens.

8. An ultrasonic probe as claimed in claim 1, wherein the reflecting mirror is a convex ultrasonic mirror for reflecting the focused ultrasonic wave.

9. An ultrasonic probe as claimed in claim 1, wherein the reflecting mirror is a concave ultrasonic mirror for reflecting the focused ultrasonic wave.

10. An ultrasonic probe as claimed in claim 1, wherein the focusing element is an acoustic lens having aspheric surface.

11. An ultrasonic probe as claimed in claim 1, wherein the reflecting mirror is a convex ultrasonic mirror, the focusing element is an acoustic lens having an aspheric surface, and the convex ultrasonic mirror is an aspherical mirror having two different curvatures.

12. An ultrasonic probe as claimed in claim 1, wherein the reflecting mirror is a concave ultrasonic mirror, the focusing element is an acoustic lens having an aspheric surface, and the concave ultrasonic mirror is an aspherical mirror having two different curvatures.

13. An ultrasonic probe as claimed in claim 1, wherein the reflecting mirror has a central axis of rotation passing through a center of gravity of the reflecting mirror.

14. An ultrasonic probe as claimed in claim 1, further comprising means for rotating the reflecting mirror relative to the ultrasonic wave generating means and the focusing element.

* * * * *